United States Patent
Cg et al.

(10) Patent No.: US 11,436,007 B2
(45) Date of Patent: Sep. 6, 2022

(54) PERFORMING CONFIGURATION VALIDATION TO OPTIMIZE SYSTEM FUNCTIONALITY

(71) Applicant: CERNER INNOVATION, INC., Kansas City, KS (US)

(72) Inventors: Bhuvaneshwari Cg, Bangalore (IN); Vikram Nandwani, Bangalore (IN); Kiran Kumar Bhojaraja, Bangalore (IN); Premjit Adhikary, Bangalore (IN); Palak Goyal, Jaipur (IN)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 17/130,472

(22) Filed: Dec. 22, 2020

(65) Prior Publication Data
US 2022/0197632 A1 Jun. 23, 2022

(51) Int. Cl.
G06F 9/44 (2018.01)
G06F 8/71 (2018.01)
G16H 40/40 (2018.01)
G06F 8/61 (2018.01)
G06F 8/65 (2018.01)

(52) U.S. Cl.
CPC .............. *G06F 8/71* (2013.01); *G06F 8/62* (2013.01); *G06F 8/65* (2013.01); *G16H 40/40* (2018.01)

(58) Field of Classification Search
None
See application file for complete search history.

(56) References Cited

U.S. PATENT DOCUMENTS

| 6,002,868 | A  | * | 12/1999 | Jenkins  | G06F 11/263 702/118 |
| 6,360,334 | B1 | * | 3/2002  | Kavanagh | G06F 8/61 707/999.006 |
| 6,880,107 | B1 | * | 4/2005  | Kraft, IV | G06F 11/08 713/2 |
| 8,291,378 | B2 | * | 10/2012 | Arnold   | G06F 8/61 717/106 |

(Continued)

OTHER PUBLICATIONS

Wolgang Fleisch, "Applying Use Cases for the Requirements Validation of Component-Based Real-Time Software", 1999 (Year: 1999).*

*Primary Examiner* — Wei Y Zhen
*Assistant Examiner* — Lanny N Ung
(74) *Attorney, Agent, or Firm* — Shook, Hardy & Bacon L.L.P.

(57) ABSTRACT

Methods, systems, and computer-storage media are provided for validating the configuration of one or more applications to be used by one or more users in a healthcare management system. Requests are received to perform a configuration validation for at least one application at a first location. Configuration file data comprising one or more requirements and configuration data for the at least one application is obtained. The configuration validation is performed by conducting a comparative analysis on the configuration file data and the configuration data. If the data is identical, then the requirements are met, and the correct version of the application is installed. If the data is not identical, then the system identifies the correct version that needs to be installed. A message is generated for the first user comprising the configuration validation outcome.

20 Claims, 10 Drawing Sheets

(56) References Cited

U.S. PATENT DOCUMENTS

| | | | | |
|---|---|---|---|---|
| 10,839,351 | B1* | 11/2020 | Sura | G06Q 10/103 |
| 2006/0048141 | A1* | 3/2006 | Persson | G06F 8/61 |
| | | | | 717/176 |
| 2010/0100875 | A1* | 4/2010 | Bastien | G06F 11/2289 |
| | | | | 717/168 |
| 2012/0324417 | A1* | 12/2012 | Somani | G06F 9/44 |
| | | | | 717/101 |
| 2014/0380278 | A1* | 12/2014 | Dayan | G06F 11/3692 |
| | | | | 717/124 |
| 2015/0058679 | A1* | 2/2015 | Jackson | G06F 11/3433 |
| | | | | 714/47.2 |
| 2015/0195182 | A1* | 7/2015 | Mathur | H04L 41/0866 |
| | | | | 714/27 |
| 2016/0224554 | A1* | 8/2016 | Yu | G06F 40/14 |
| 2017/0019314 | A1* | 1/2017 | Chieu | H04L 41/5054 |

* cited by examiner

```
FILE  EDIT  VIEW  FAVORITES  TOOLS  HELP

RADCONFIG.JSON

1  {
 2    "CLIENT THIN" : {
 3      "APPLICATION A" : {
 4        "SOFTWARE" :
 5        [{
 6          " APPLICATION A1 ":"2.0.14.0", "APPLICATION A2 | REPORTING – INTEGRATION COMPONENT (X64) ":
 7          "6.6.81.0", "APPLICATION A3 | REPORTING – INTEGRATION COMPONENT (X86) " : "6.6.81.0"
 8        }]
 9      }
10    },
11    "SERVER THIN" : {
12      "APPLICATION A" : {
13        "SOFTWARE" : [{
14          "APPLICATION A2 X64" : "2.0.19.0"
15        }]
16      }
17    },
18    "FAT" : {
19      "APPLICATION A" : {
20        "SOFTWARE" : [{
21          "APPLICATION A3 | REPORTING – INTEGRATION COMPONENT (X64) " " "6.6.81.0"
22        }]
23      "UNEXPECTEDSOFTWARE" : [{
24          "APPLICATION X" : "2.0.19.0", "APPLICATION Y X64" : "2.0.19.0"
25        }]
26      }
27  }
```

*FIG. 5.*

PERFORMING CONFIGURATION VALIDATION TO OPTIMIZE SYSTEM FUNCTIONALITY

BACKGROUND

Software technology has significantly progressed over the last several decades and as new innovations in technology arise, systems utilizing various software technology require updates to maintain functionality. Healthcare systems rely heavily on complex computer systems and servers to communicate and store critical information. As technology has progressed, the cost of healthcare has increased significantly and the management of individual healthcare has become more complex. In order to maintain effective and efficient systems, healthcare management systems need to ensure that applications being utilized within the healthcare management system (e.g. a hospital that may utilize numerous applications daily) are the correct version and satisfy determined requirements in order to optimize system performance. If not, users within the system may receive errors or delays when utilizing applications within the system. This may be especially critical in certain areas of medical care. For example, technology regarding the digitalization of radiological images and viewing of such images is rapidly evolving. As such, in order to provide the best viewing of radiological imaging, the systems being utilized by a healthcare provider, such as a radiologist, need to be validated to determine whether the correct version of the application to be used is installed and whether all requirements are satisfied. If not, then the healthcare provider may encounter delays, errors, or diminished quality for the data requested, which in turn could impact the medical care for an individual. As such, the validation of the configuration of applications, such as image viewing applications, is important.

Additionally, maintaining healthcare management systems is a complex task requiring significant resources and manpower. The cost of operating numerous applications within a system is high. Often times, when an application or an entire system is updated with new technology or changes to the present technology, there is a lack of validation prior to users using the updated applications. As such, in some instances, users may encounter issues, which then have to be addressed and can cause further complications when an application is being utilized by multiple people within a healthcare management system at various locations. Therefore, a more proactive system in which an application's configuration at a specific location can be validated proactively may lead to a decrease in the manpower required to fix an issue at a later time and decrease the cost associated with managing the healthcare management system. Additionally, proactive configuration validation would ensure that when an application is utilized, the correct version is installed, leading to a better user experience.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Various types of applications are utilized simultaneously within a healthcare management system and require different resources. Within a healthcare management system, different healthcare providers utilize different types of technology in order to provide medical care to individuals. For example, radiologists require software and applications which allow them to review different types of radiological images that vary in complexity. Maintaining the software and applications both at server locations, clinical locations, and remotely is important to ensuring that the needs of users are met and that applications are running effectively and efficiently within the system.

Generally, as applications and software receive upgrades at various locations within the healthcare management system, including but not limited to clinical sites (e.g. hospitals), on laptops utilized by healthcare providers, and on remote and local servers, applications are not always individually validated. Each individual user interface within the system may have different capabilities and requirements in order to function optimally. As such, the requirements for a specific application could potentially vary from location to location. For example, based on the specifications of the user interface, a newer or older version of an application might be required. Additionally, in many systems, as upgrades occur, the whole healthcare system will be required to update to the newest version of an application. Ensuring that the correct version of an application is installed and being utilized may also be important for communication between user devices within a healthcare management system.

Historically, configuration validation was not proactively conducted. Instead, as users ran into problems with applications, such applications were retroactively analyzed to determine if the correct version of the application was installed prior to checking for other issues. However, in order to save time, resources, and cost, a proactive system in which a request or triggering event proactively initiates the configuration validation of an application at a location is useful. If a user, such as an administrator, requests a configuration validation of a selected application at a specific location after an update is completed on the whole system, it provides the opportunity to ensure that the application meets the necessary requirements prior to any users, such as healthcare providers, utilizing the application and facing any potential challenges. Therefore, a system that provides configuration validation to determine whether a correct version of an application is installed and also identifies the required version when the current version is not correct is an improvement to prior systems and will help with the maintaining an effective and efficient healthcare management system.

At a high level, the present disclosure discloses systems and methods for validating the configuration of one or more applications at one or more locations. The features of selected applications are validated to ensure the required version of the application is utilized by the system. Configuration validation may take place on a predetermined schedule, at the time of general system updates, or as needed by a user. For example, if a system has recently received software updates and a healthcare provider is utilizing a device remotely, the application used by the healthcare provider to view radiological images may no longer be the version of the application required by the system. As such, configuration validation can be performed on the application in order to determine whether the application meets the systems requirements. If the application does not meet system requirements, the system can generate messages to a user to update the application or take other actions, such as removing a component found on the user's system that is harmful or not needed.

Aspects herein describe computer-storage media, computerized methods, and computing systems that are useful in a computer healthcare system by providing configuration validation to one or more applications to be used by one or more users. The system receives an indication to perform a configuration validation for at least one application at a first location. Then the system accesses a first source to obtain configuration file data comprising one or more requirements for the at least one application. The system also accesses the at least one application to obtain configuration data for the at least one application. Then, the system performs configuration validation on the at least one application by analyzing the configuration file data comprising the one or more requirements and the configuration data from the at least one application to determine whether the requirements are satisfied. Once the configuration validation is complete, the system generates a message to a first user, via the first user interface, indicating the outcome of the configuration validation.

There are multiple different outcomes for the configuration validation performed. If the system determines that the one or more requirements are satisfied, that indicates that the configuration file data and the configuration data for the at least one application are identical and the correct version of the application is presently installed. By contrast, if the configuration file data and the configuration data for the application are not identical, then the requirements are not satisfied, and the message generated to the first user will indicate that the version of the at least one application is not the required version. The required version of the application will be noted in the message so that the first user can use this information to update the application to satisfy the one or more requirements. It is also contemplated that during the configuration validation process, the system may identify one or more unexpected applications. As used herein, an unexpected application is an application determined as unnecessary or undesired. For example, an unexpected application may be an old version of an application or an application that is present that might interfere with the intended use of the application identified for verification. This information will also be relayed to the first user in the message generated along with instructions on what do with the unexpected application.

As well, aspects herein are also directed to a system that comprises a database comprising one or more configuration files comprising data regarding one or more requirements for at least one application. The system also comprises one or more processors and a storage device storing a computer program product comprising computer instructions that, upon execution by the one or more processors, cause the one or more processors to perform operations comprising receiving, from a first user, an indication to perform a configuration validation for the at least one application at a first location based on a selection of the at least one application and first location by the first user. Then, one or more configuration files from the database are obtained to perform configuration validation of the at least one application. The system then determines whether the at least one application is installed at the first location. If it is determined that the at least one application is not installed at the first location, a message is generated to the first user, via a first user interface, indicating that the at least one application is not installed at the first location. If the system determines that the at least one application is installed at the first location, it then receives configuration data for the at least one application and performs configuration validation on the at least one application, wherein the configuration validation compares the configuration file data and the configuration data for the at least one application to determine if the configuration file data and the configuration data for the at least one application are identical. Once the configuration validation is completed, a message is generated to the first user, via the first user interface, comprising the configuration validation outcome.

BRIEF DESCRIPTION OF THE DRAWINGS

Embodiments are described in detail below with reference to the attached drawings figures, wherein:

FIG. 5 illustrates an example JSON file illustrating the configuration file data comprising one or more requirements;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for validating the configuration of one or more applications to be used by one or more users in a healthcare management system, After receiving a request or indication perform configuration validation on a selected application at a selected location, an analysis of configuration data for an application and configuration file data comprising one or more requirements is analyzed. As used herein, an indication or request received may include, but is not limited to, a request to perform a configuration validation received from a user or other source, an indication that an identified time to perform configuration validation within a predetermined schedule has occurred, or an indication to initiate an automatic configuration validation. The outcome of the configuration validation is transmitted to a user via a message, which may also include additional action items such as installing or uninstalling specified software.

As used herein, the term facility, may be any facility which provides healthcare to an individual such as, but not limited to, a hospital, acute care facility, rehabilitation facility, urgent care facilities and the like. Additionally, the term "receiver" refers to a component within a computing system which is receiving data, requests, communication, or other information from another source. For example, as used herein, a receiver is configured to receive requests to obtain certain data or complete certain tasks.

Figure 1:
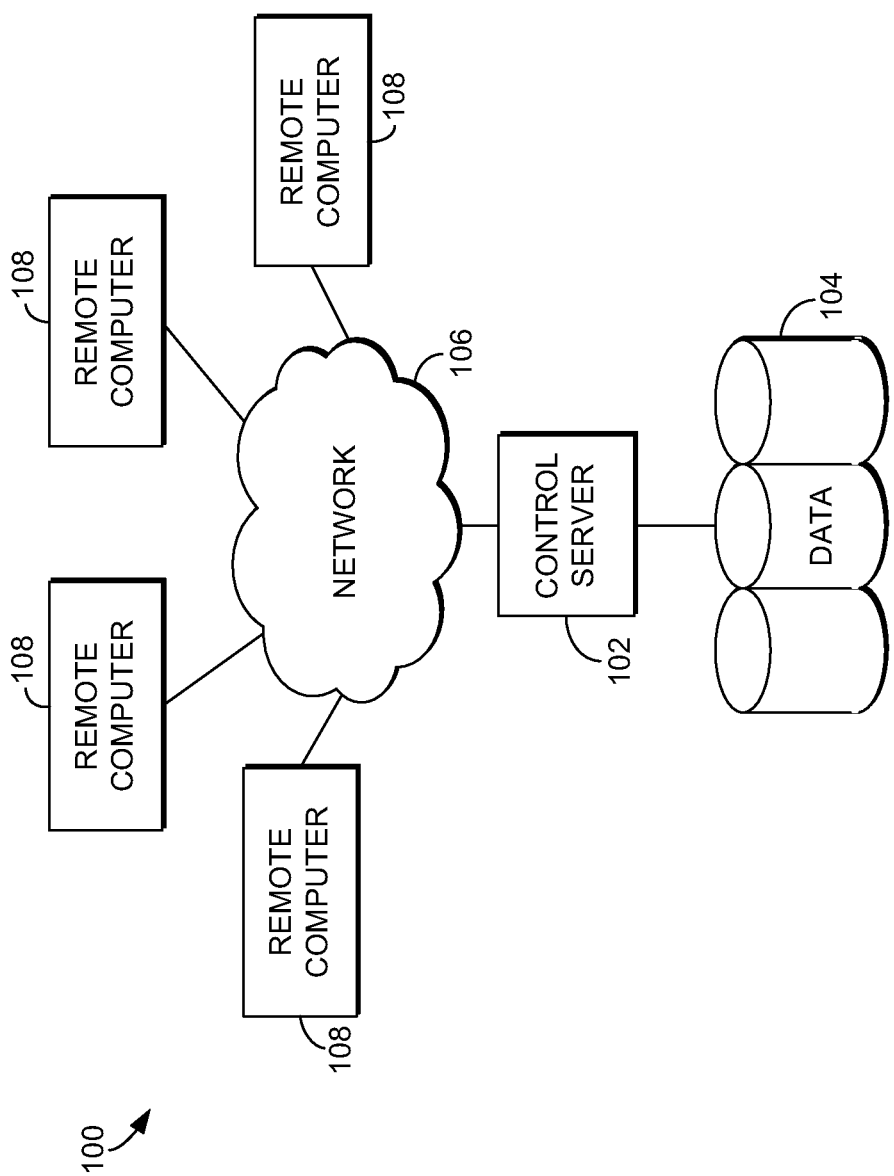
FIG. 1 is a block diagram of an exemplary computing environment suitable to implement embodiments of the present invention.

An exemplary computing environment 100 suitable for use in implementing embodiments of the present invention is described below. FIG. 1 is an exemplary computing environment (e.g., medical-information computing-system environment) with which embodiments of the present invention may be implemented. The computing environment 100 is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present invention. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present invention to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and medical information workflows. The remote computers might also be physically located in traditional and nontraditional medical/healthcare care environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Health care providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
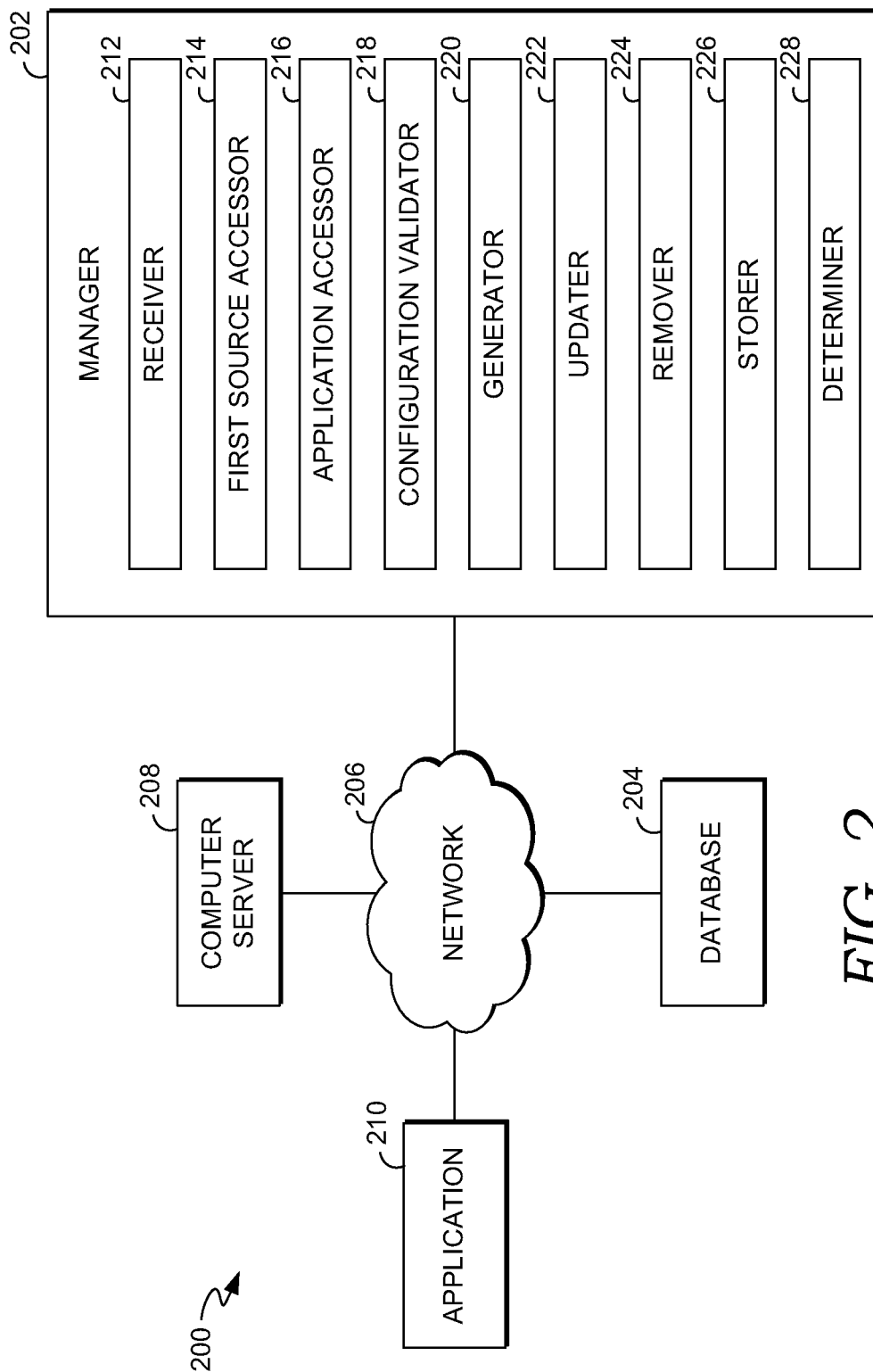
FIG. 2 is an example system architecture suitable to implement embodiments of the present invention.

Turning now to FIG. 2, an exemplary computing system 200 is depicted. The computing system 200 (hereinafter "system") is merely an example of one suitable computing system and is not intended to suggest any limitation as to the scope of use or functionality of embodiments of the present invention. Neither should the system 200 be interpreted as having any dependency or requirement related to any single component or combination of components illustrated herein.

In some embodiments, one or more of the illustrated components may be implemented as a stand-alone application. The components described are exemplary in nature and in number and should not be construed as limiting. Any number of components may be employed to achieve the desired functionality within the scope of the embodiments hereof. Further, components may be located on any number of servers.

In the embodiment shown in FIG. 2, the system 200 includes a manager 202, database 204, network 206, computer server 208, and application 210. While FIG. 2 illustrates only one computer server 208, it is contemplated that the system 200 may comprise any number of servers 208.

The application 210 may be any type of application that might be used by a user in order to display, review, or analyze data. For example, the application 210 might be an electronic medical record (EMR) that is comprised of in exemplary aspects, medication information, vital sign information, physician orders, demographic information, laboratory and/or procedure values and results, medical history (symptoms, diagnoses, and the like), medication history, medical procedure history, treatment history, number of readmissions and causes for readmission, social determinants (health literacy, behavioral factors, support network, and the like), assessment information for the individual, and any other pertinent medical data monitored by a healthcare system. In some aspects, the application 210 may be an image display application, such as a Picture Archiving Communication System (PACS). It is also contemplated that the application might be a larger healthcare management solution that comprises various features including an EMR, image viewer, dictation tool, and etc. A healthcare provider, such as a radiologist, may use application 210 to request to view an image, view the requested image, and then input medical diagnosis and any other notes.

Generally, the manager 202 is configured to provide configuration validation of one or more applications 210. In this embodiment, the manager 202 includes a receiver 212, a first source accessor 214, an application accessor 216, a configuration validator 218, a generator 220, an updater 222, a remover 224, a storer 226, and a determiner 228. In this aspect, the manager 202 is comprised of nine subcomponents (listed above). However, in other aspects, the manager 202 may be comprised of more or less components and any and all variations are contemplated herein. The components described are exemplary in nature and in number and should not be construed as limited. Any number of components may employed to achieve the desired functionality within the scope of the embodiments hereof.

Additionally, in some aspects, the manager 202 may also be located within the database 204. It will be appreciated that some or all of the subcomponents of the manager 202 may be accessed via the network 206 and may reside on one or more devices. Further, while system 200 is comprised of one manager 202, it is contemplated that the system 200 may include more than one manager 202. It is also contemplated that the manager may be integrated into the application 210.

The receiver 212 within the manager 202 is configured to receive a request to perform a configuration validation for at least one application at a first location. The request may be received from a user, via a user interface. For example, a healthcare system administrator may initiate a request to validate at least one application 210 at a first location to determine whether the application 210 is the correct version (e.g., an intended, desired, and/or current version) and operating effectively. In other instances, the receiver 212 may receive the request to perform a configuration validation on a predetermined schedule assigned by the system 200. Such requests might be received on a weekly, daily, or monthly basis. It is also contemplated that the requests may be received by the receiver 212 when the system 200 undergoes updates to confirm that an application, such as application 210, is installed correctly, which includes determining if the required version of the application 210 is installed and functioning. Further, the requests to perform a configuration validation may occur in response to triggering events. For example, a user may try to use application 210 to view a medical image, and encounters an issue or determines that the application 210 is not performing at the required speed. As such, the user may submit a request for configuration validation directly to the receiver 212 or if the user is a healthcare provider, may submit a request to a system administer, who may then initiate a request for configuration validation of the application 210 based on the reported issue. Additionally, in aspects, the request received by receiver 212 may be received from a local requester or from a remote requester or by the system 200 itself.

When the receiver 212 receives the request to perform a configuration validation for at least one application at a first location, the request received will include information regarding which application is to be validated and identify a first location. Because healthcare management systems comprise multiple different applications, the requestor will select which application is to be validated. For example, the requestor may select that a digital dictation application to undergo configuration validation. Then the requestor will select the location, which may be at the healthcare system's server, a client's server, or on a comprehensive server, for example. Additionally, the receiver 212 may receive more than one request to perform a configuration validation. The receiver 212 can receive requests to perform configuration validation for multiple applications (e.g. digital dictation and scribe) at more than one location. For example, the receiver 212 may receive a request to perform a configuration validation for an application and digital dictation application at both the healthcare management system's server and a client server. The requests may be received simultaneously or at different times.

Next, the first source accessor 214 accesses a first source to obtain configuration file data that comprises one or more requirements for the at least one application. The first source that is accessed by the first source accessor 214 may be a local or remote database, another application, or any other source that is configured to store configuration file data. Configuration file data is data that describes the one or more requirements that must be satisfied for an application to validated. Such requirements may be stored in a variety of file formats, such as a JSON file. The requirements outlined in the configuration file data will include items such as the type of application or feature, version number, number of components, registry key value, function and any other relevant features.

The application accessor 216 will access the at least one application to obtain configuration data for the at least one application. When the application accessor 216 accesses the at least one application, it will target the requirements indicated from the configuration file data. As such, in some instances, the application accessor 216 will only obtain specific configuration data related to the at least one application such as the application version number or name. In other instances, the application accessor 216 may obtain all data related to the configuration of the application, even though only specific data related to the one or more requirements from the configuration file data will be analyzed.

Based on receiving the configuration file data from the first source and the configuration data from the at least one application 210, the configuration validator 218 will perform a configuration validation on the at least one application. When performing the configuration validation, the configuration validator 218 conducts a comparative analysis between the configuration file data and the configuration data obtained from the application to determine whether the one or more requirements have been satisfied. In order to complete this analysis, the configuration validator 218 compares the data, such as the file name and version, from the configuration file data to the same data from the application 210. The configuration validator 218 will compare the data regarding the application 210 name, version, and function indicated as required from the configuration file data to see if it is identical to or matches the configuration data obtained from the application. The first source accessor 214 may access a database, such as database 204, to obtain configuration file data comprising requirements such as the application name, version, and function of the application. The application accessor 216 will obtain the configuration data for the application to be validated including the application's name, version, and function. Then, the configuration validator 218 will analyze and compare the data from the first source (e.g. the name, version, function of the application identified as a requirement) and the configuration data from the application (e.g. the name of the application, version, and function). If the configuration data from the first source and the application, which may be formatted in any acceptable file format, such as JSON, are found to be identical, then the requirements have been satisfied. If they are not identical, then the requirements have not been satisfied.

The determination of the configuration validation performed can have multiple outcomes. Regardless of the outcome of the configuration validation performed, a validated output, such as a message, is generated to a first user by the generator 220, via the first user's interface, indicating the outcome. If it is determined that the one or more requirements are satisfied by the configuration validator 218, the generator 220 will generate a message to the user indicating that the requirements were met. The message may contain additional detail such as confirming that the correct version of the application 210 was installed and identifying the version. In instances where the configuration validator 218 determines that the one or more requirements have not been satisfied, the configuration file data and the configuration data from the at least one application 210 were determined not to be identical. Therefore, the message generated by the generator 220 will indicate that the appropriate/correct version of the application 210 has not been installed and identify the appropriate/correct version to install. Further, it is contemplated that the generator 220 may also include a link that the user may use in order to update the application 210 to the correct version. If this occurs, it is contemplated that the system 200 may perform a second configuration validation at a subsequent time in order to confirm that the user has correctly installed the required version and that the configuration file data and the configuration data for the at least one application 210 are identical. Additionally, in some aspects, after the generator 220 generates the message indicating that the correct version is not present, the system, via an updater 222, may automatically update the application 210 to the appropriate/correct version. The updater 222 is configured to update the application 210 to the appropriate/correct version and may act based on a command from the configuration validator 218 or a user.

There may also be instances in which the configuration validator 218 may determine that the one or more requirements are met, but may also identify some unexpected software or application, such as an additional application or driver, that is not needed or should not be present (e.g., which can cause additional problems or issues in the operation of the application, or which are extraneous). In this case, the generator 220 will generate a message that indicates that the correct version of the application validated is present and will also identify the unexpected software found with a request to uninstall such software. It is contemplated that the user can be provided with the option to manually uninstall the undesired software or the system 200 may utilize a remover 224 to remove the unwanted software automatically after the message is generated to the user. The remover 224 is configured to receive commands from the configuration validator 218, user, or any other source capable of communicating via network 206.

Once the configuration validation process has been completed, in some instances, a storer 226 may store the outcome and any messages transmitted to a user on a database, such as database 204. This information may be stored for future use and analysis as administrators or system engineers continue to provide updates or improvements to the system 200.

It is further contemplated that, in some aspects, the receiver 212 can receive requests to perform configuration validation for more than one application 210, at more than one location, and from more than one user. Unlike previous systems, the present system will allow configuration validation of at least one application 210 in an efficient and effective manner in order to decrease or eliminate the occurrence of an application not functioning as needed by a user or not performing adequately. The configuration validation of the present system will create a more efficient system. Additionally, in some aspects, a second validation configuration may take place to confirm that the identified action, such as removing an undesired application or version, has occurred.

In yet some other aspects, prior to the configuration validator performing configuration validation on the application 210, the determiner 228 may first determine whether the application 210 is even installed at the location selected. In this case, the determiner 228 validates the application 210 name after the application accessor 216 has obtained the configuration data for the application. If the determiner 228 determines that the application 210 is not installed based on the absence of an application having the correct name at the location selected, then the generator 220 will generate a message to the user stating that the requested application 210 is not currently installed at the selected location. The user can then install the required version of the application 210, if desired. If the determiner 228 determines that the application 210 is installed, then the configuration validator 218 proceeds with its comparative analysis of the configuration file data and the configuration data from the application 210 to determine whether the requirements are satisfied. The generator 220 can then generate a second message indicating the outcome of the configuration validation.

Figure 3:
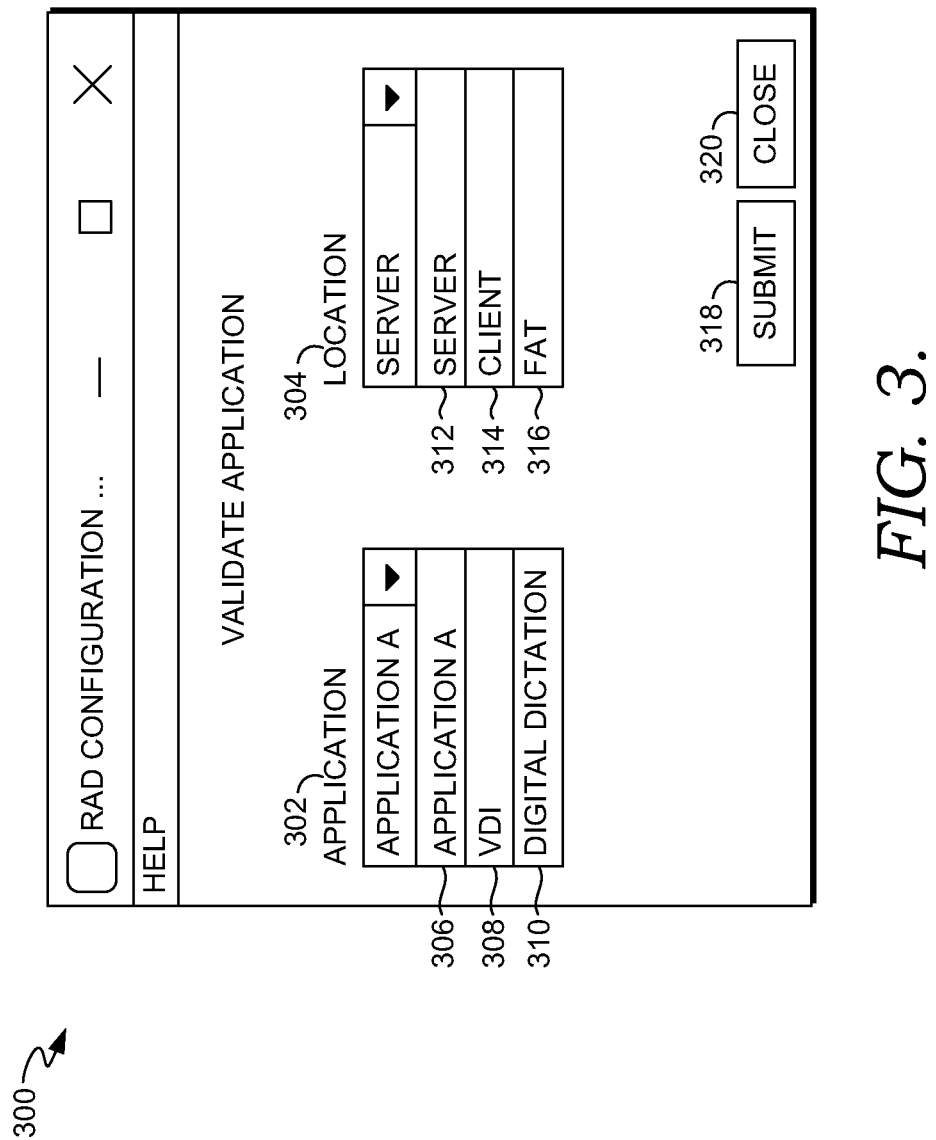
FIG. 3 illustrates an example configuration validation infrastructure provided to a user.

Next, FIG. 3 illustrates an example configuration validator request interface 300. As shown, there are two drop down selections from which the requester can initiate the request for a configuration validation. First, the requestor can select the application 302 to be validated. In this example, there are three options to choose from: Application A 306, virtual desktop infrastructure (VDI) 308, and digital dictation 310. While the example drop down menu shown in FIG. 3 provides three potential applications to be selected, there may be fewer or more potential features or applications to that can be selected by a requester.

In addition to selecting the application or feature type, the requester must also select the location or setup type for the configuration validation. In this case, the requestor has three options: server 312, client 314, or FAT 316. When a user selects the location as server 312, the configuration validation will be performed on the healthcare system's server. By contrast, if client 314 is selected, then the configuration validation will be performed on the client's device, such as a client laptop. The third option, FAT 316, is when all programs are run on a single comprehensive system. Once the requester selects the application 302 and location 304, they will click on the submit button 318, which then sends the request to the receiver 212. As multiple choices are given for the application 302 and location 304, it is possible for the requester to request the validation of multiple applications at different locations.

Figure 4A:
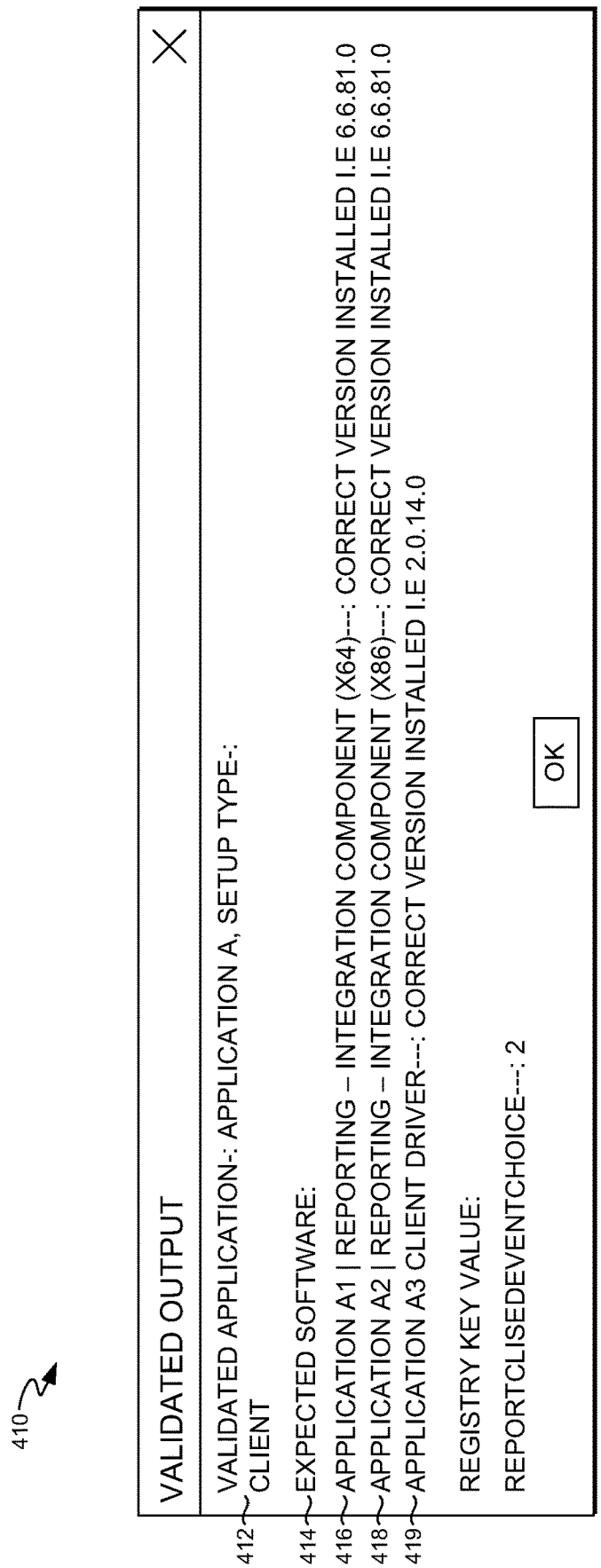
FIG. 4A illustrates an example of the results of a configuration validation.
Figure 4B:
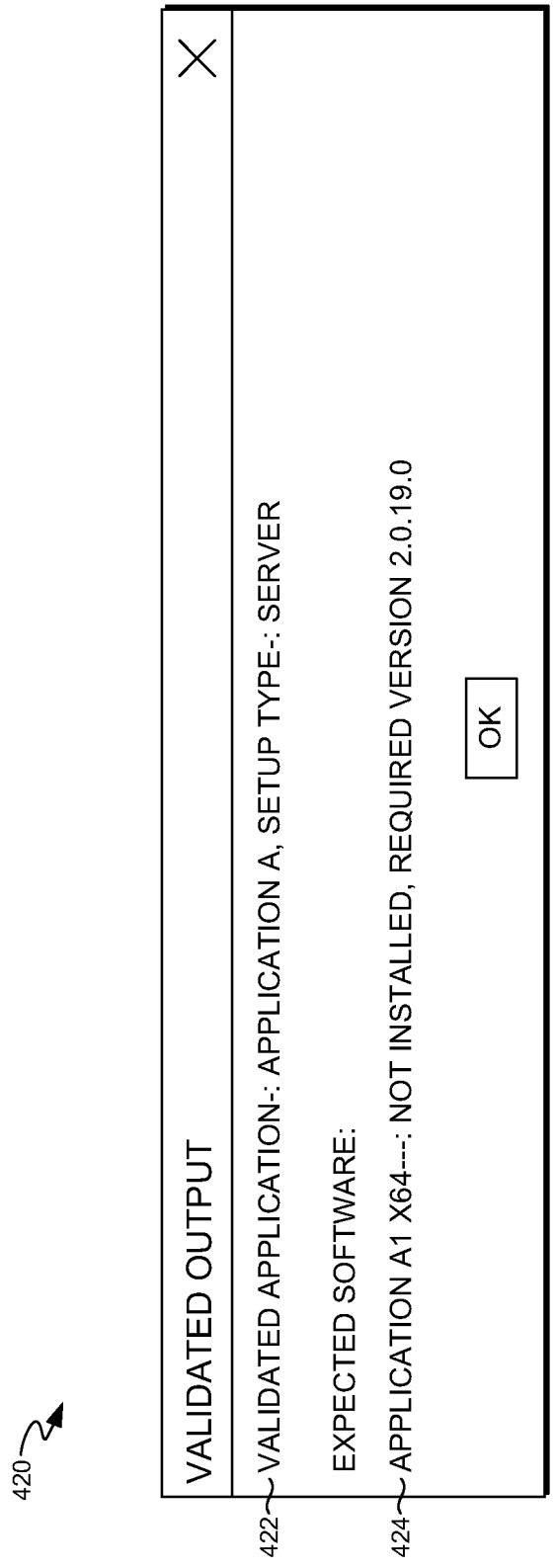
FIG. 4B illustrates another example of the results of a configuration validation.
Figure 4C:
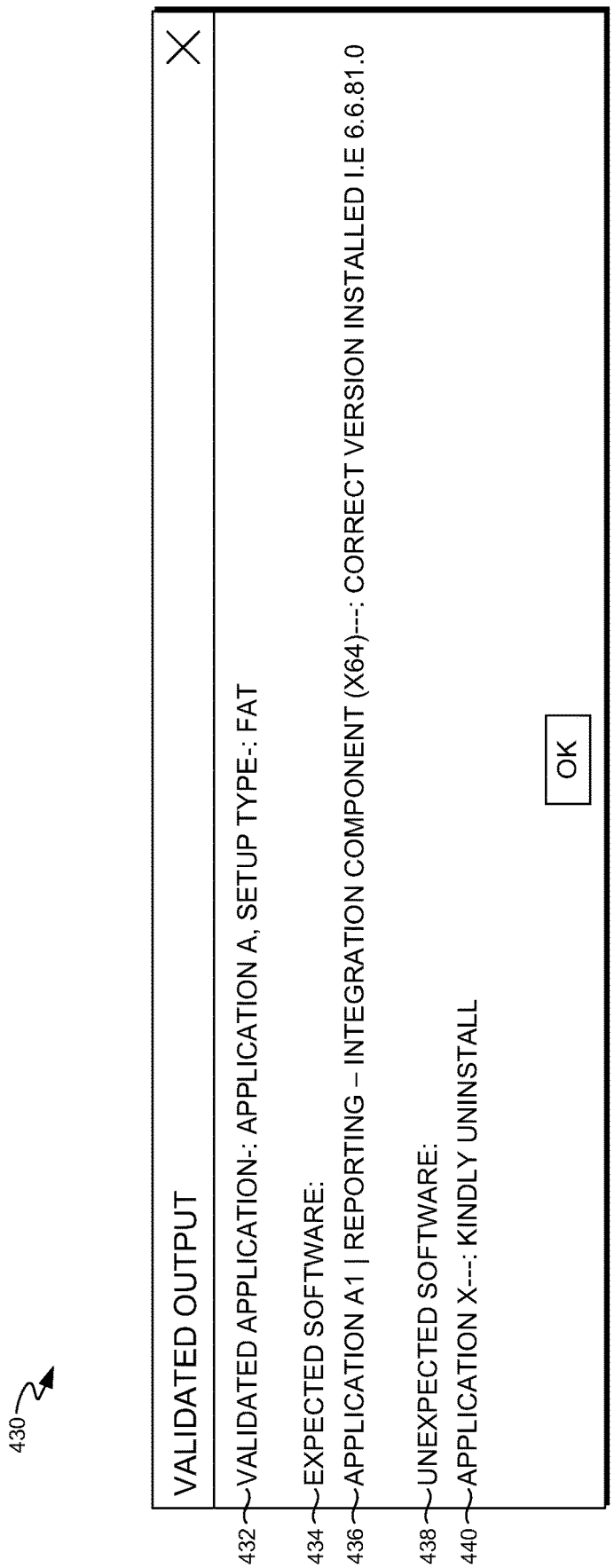
FIG. 4C illustrates another example of the results of a configuration validation.

FIGS. 4A-4C illustrate different potential messages generated by generator 220 with the outcomes from the configuration validation completed by the system 200. Beginning with FIG. 4A, an example validation output message 410 is depicted. In this example, the message first indicates what application and location where the configuration validation was completed at line 412. In this case, the application that was selected for validation was Application A and the location of the feature was at the client server. Under the expected software category 414, three items are listed: Application A1 416, Application A2 418, Application A3 419, which represent the one or more requirements for Application A that underwent configuration validation. In order to have determined the expected software 414 that is presently installed at the client server, the first source accessor 214 accessed a first source, such as a database, to obtain configuration file data that comprised the one or more requirements for Application A. The application accessor 216 also accessed Application A at the client server in order to obtain the configuration data related to the three items 416, 418, and 420. The configuration validator 218 then performed a comparative analysis between the data obtained from the first source and the configuration data obtained from Application A at the client server.

In the message 410 generated depicting the outcome of the configuration validation, the results of the configuration validation are noted for all three items 416, 418, and 419. As shown, the configuration validator determined that the configuration data was identical to the configuration file data for Application A1 416, Application A2 418, and Application A3 419. As such, the configuration validator concluded that the correct version has been installed for each item. The message 410 will be generated on a user interface and the user can review message 410 and take relevant action afterward. For example, if a system update triggered the needed for configuration validation, the user is now able to confirm that the correct version of Application A is installed and as such, can proceed with additional validations or approvals to utilize the application. Once the user has reviewed the message 410, the user can click on the "ok" button and proceed back to the interface shown in FIG. 3 to select additional applications for validation, as needed.

FIG. 4B illustrates another example validated output message 420. In this message, the receiver 212 had received a request to perform configuration validation on the Application A is again shown in line 422. However, the location selected is at the system's server. In this message, the outcome of the configuration validation is that the Application A1 424 is not installed. As such, the configuration file data and the configuration data for the application at the system's server were not identical when the configuration validator 218 performed a comparative analysis and therefore, the requirements for the application were not satisfied. As discussed, when the outcome of the configuration validation indicates that the requirements are not satisfied (e.g. configuration file data and the configuration data for the at least one application are not identical), the validated output message 420 states that the expected software—Application A1 424 is not installed. Additionally, the message 420 also states the required version that is needed. In this case, required version needed is "2.0.19.0." Upon receiving the message 410, the user can install the required version noted so that Application A is run effectively on the system's server.

As seen in FIGS. 4A and 4B, the outcome of performing configuration validation on the same application, but at two different locations, may be different. By performing configuration validation for the same application that may be used at multiple locations, the system 200 will be optimized so that each server or location has the required version of an application to function most effectively. Such variation in outcomes may be due to each location's capacity and features. For example, the version of an application utilized on a client's laptop may be different than the version required for the whole healthcare system's server. While not shown, it is contemplated that in some aspects, the validated output message 420 may also include a link for a user to click on to download the required version. In other aspects, after generating the report, the updater 222 may automatically update the application to the required version. Additionally, in some aspects, a second configuration validation may take place at a predetermined time after the message 420 is generated to ensure that the correct version has been installed. It is also contemplated that in this case, the generator 220 can send additional messages to the user reminding the user of the outcome of the configuration validation and any additional action that must take place.

FIG. 4C illustrates another example of a validation output message 430 generated by generator 220 after configuration validation has been performed. Similar to FIGS. 4A and 4B, the validated application 432 and expected software 434 are listed. In this message, the configuration validator determined that the version of Application A1 is the correct version and notes the version installed at 436. However, in addition to validating the configuration of Application A, the configuration validator has also identified an unexpected software 438. In this case, the unexpected software is Application X 440, which the message 430 states should be uninstalled. The configuration validator 218 may determine that the Application X 440 should be uninstalled because, for example, it is interrupting the function of the Application A, is outdated, may be taking up storage space, or is not functioning properly. In some instances, the user may be provided with a link to click on to uninstall the unexpected software. In other instances, the system 200 may automatically remove the unexpected software, via remover 224. The remover 224 is configured to remove any applications or software that are indicated for removal by the system 200 or through the configuration validation process. When this is done, the generator 220 may generate a second message to the user indicating that the unexpected software has been uninstalled.

FIG. 5 illustrates an exemplary JSON file comprising the validation configuration discussed herein. The data shown in JSON file 500 is the configuration file data that the first source accessor 214 obtains in order to perform the configuration validation. As such, the information in lines 12-24 describe the one or more requirements for the at least one application. As shown in line 2, the location is at the client site and the application (shown in line 3) is the application. Lines 6-7 describe the one or more requirements for the application at the client site, including the driver version. Lines 11-14 list the requirements for the application at the server site and lines 18-24 list the requirements for the application at the FAT location.

Figure 6:
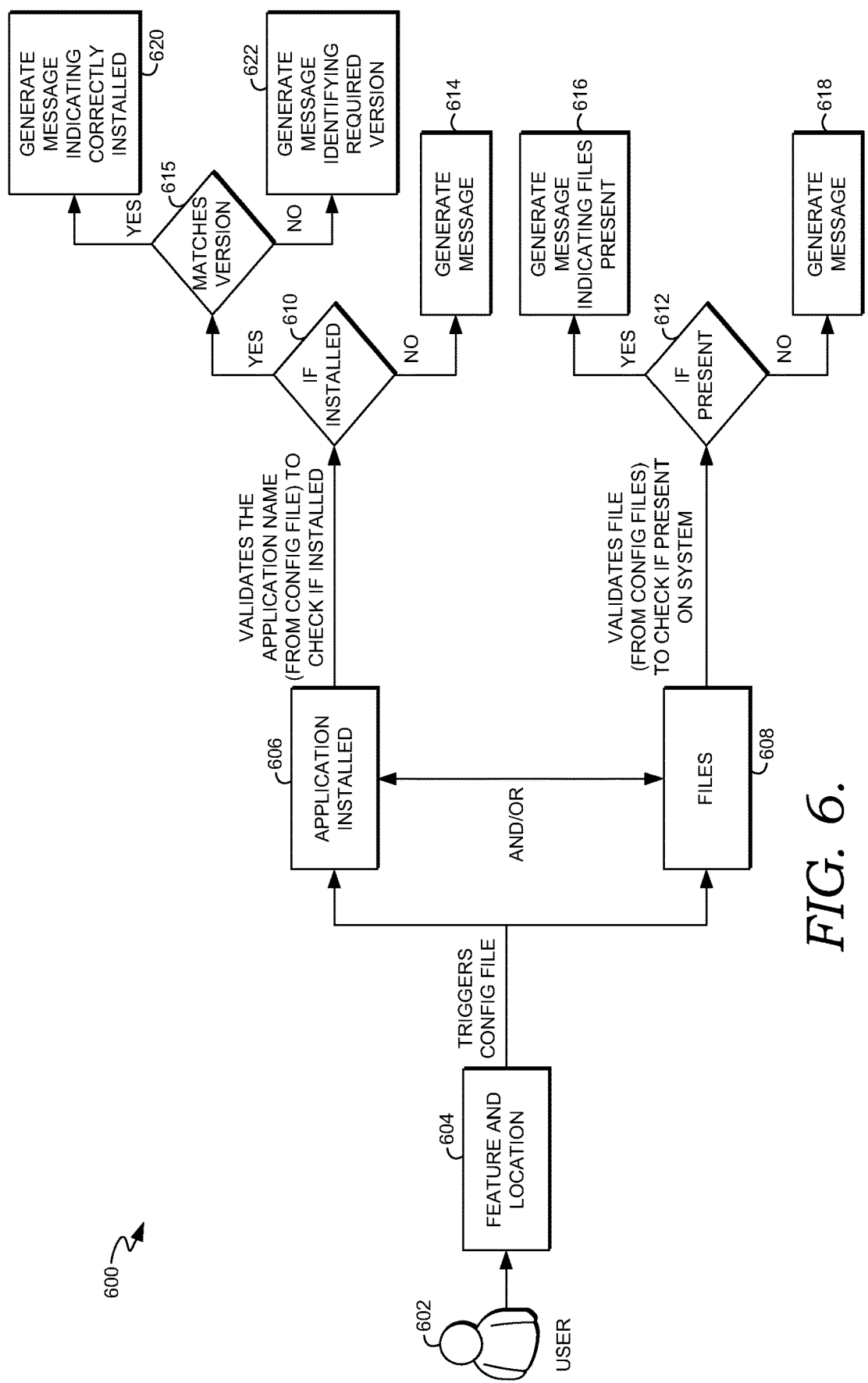
FIG. 6 illustrates an example system workflow illustrating implementation of embodiments of the present application.

FIG. 6. illustrates an example system workflow 600 illustrating implementation of embodiments of the present application. The user 602 selects the feature or application type and setup type as described in FIG. 3. When the user 602 selects the application and location, the receiver 212 receives the request to perform a configuration validation for at least one application at a first location. When the user receives the request to perform configuration validation, the request may include information about whether the configuration validation should be done on a specific application installed 606 or set of files 608. In some circumstances, the request may include a validation for both the application itself and a set of files 608. This then triggers the first source accessor 214 to access one or more configuration files to obtain configuration file data regarding the one or more requirements. The application accessor 216 will access configuration data for the application selected by user 602. At block 610, a determiner 228 determines whether the application or software is installed. In order to do this, the determiner 228 will validate the application name from the configuration data for the application that was obtained to check if the application is installed. If the determiner 228 determines that the application is installed at the first location selected for configuration validation by user 602, then the configuration validator 218 will perform a configuration validation on the application by comparing the configuration file data from a first source (e.g. a database) with the configuration data for the application. If it is determined that the data matches at 615, then the configuration validator 218 will conclude that the correct application is installed at 620. Once this determination is made, the generator 220 will generate a message to the user 602 indicating that the correct version of the software has been installed. Additionally, while not shown in the example flow diagram of FIG. 6, it is contemplated that after determining that the software is installed at 610, the generator can generate a message to the user 602 indicating this information. In other instances, the final message generated by generator 220 stating the outcome of the configuration validation can include the location verification information.

By contrast, if the configuration validator 218 determines that the configuration file data and the configuration data for the application do not match at 615, then the message generated by generator 620 will indicate that the incorrect version is not installed and will indicate the required version at step 622. Based on this information, the user can download the correct version of the application or, as mentioned, an updater 222 may automatically update the application to the required version. Additionally, if it is determined at block 610 that the application is not installed, then the generator 220 will generate a message at 614 to user 602 indicating this information. No validation can take place if the selected application is not present.

FIG. 6 also illustrates an instance in which the configuration validator validates one or more files 608 obtained from the configuration data for the first application to determine whether they are present on the system 200. If it is determined that the file is not present at 612, then the generator can generate a message to the user 602 at 618 indicating that the selected files are not present. If it is determined that the file is present at 612, then a message is generated stating that the files are present at 616.

Figure 7:
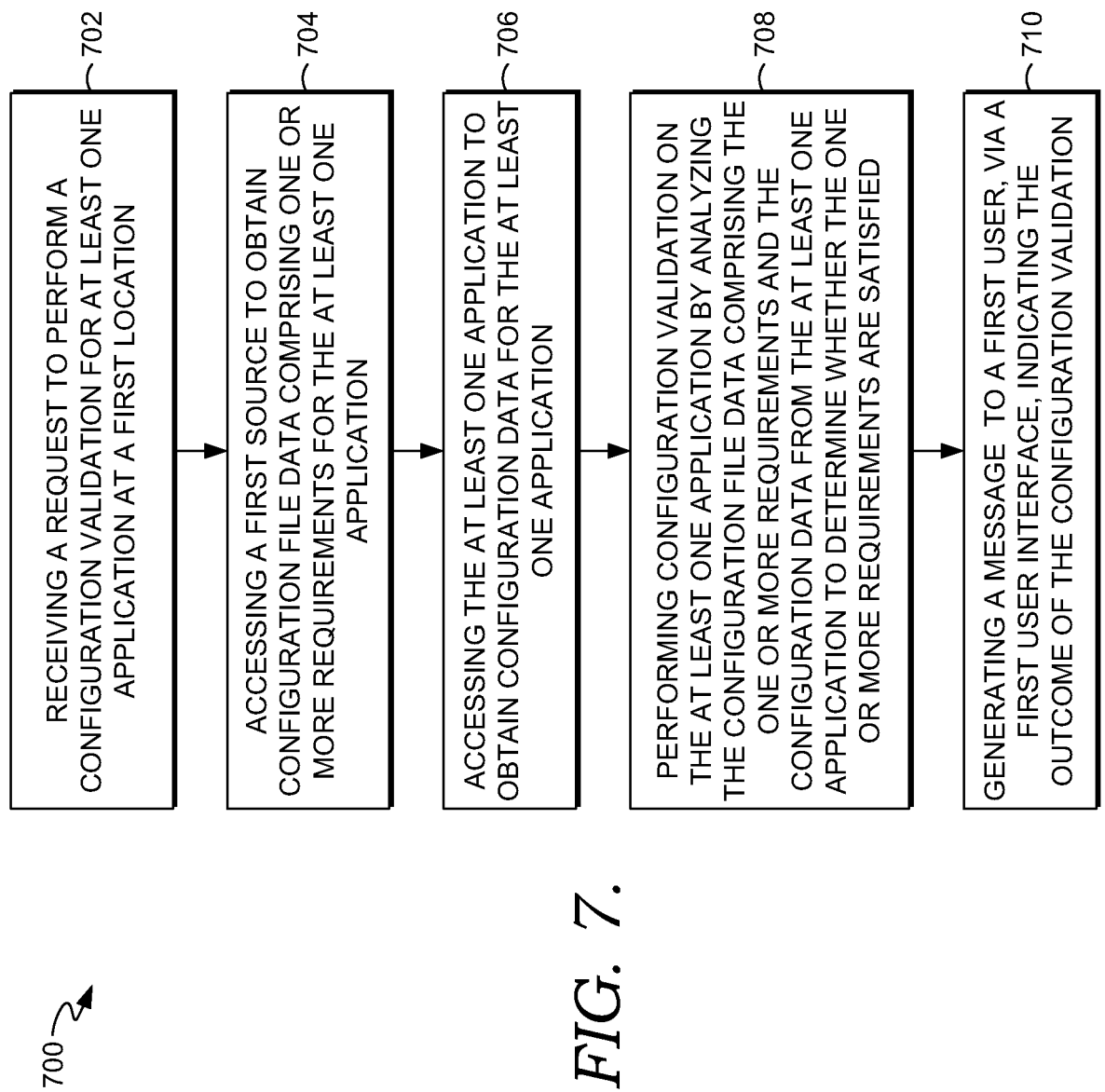
FIG. 7 is a flow diagram describing an example method of executing embodiments of the present invention.

Next, FIG. 7 illustrates a flow diagram 700 describing an exemplary method of executing embodiments of the present invention. Beginning with block 702, the receiver 212 receives a request to perform a configuration validation for at least one application at a first location. As discussed, the request might come from a system administrator, client user, or any user who may need to verify the configuration of an application. After receiving the request, the first source accessor 214 accesses a first source at 704 to obtain configuration file data comprising one or more requirements for the at least one application. These requirements may include, but are not limited to, the application name, function, and version. The application accessor 216 accesses the application selected for configuration validation to obtain configuration data for the at least one application at block 706. The configuration data for the application may include but is not limited to the name of the application, version of the application, and function of the application. The same configuration data obtained for from the first source (e.g. the data that is required) will be obtained from the application. However, the application accessor 216 may, in instances, obtain additional data as needed.

Once the configuration file data and the configuration data for the application are obtained, the configuration validator will perform a configuration validation at block 708. To complete the validation, the configuration validator 218 will analyze the configuration file data and the configuration data from the application 210 to determine whether the requirements are satisfied. For example, if the requirements are that the application name, function and version must match, then the configuration validator 218 will compare the configuration data from the application with the configuration file data to see if they are identical. The generator 220 will generate a message to a first user, via a first user interface, indicating the outcome of the configuration validation at step 710. If the one or more requirements are satisfied, the message generated will indicate that the correct version is installed. If the one or more requirements are not satisfied, then the message generated will indicate that the correct version is not installed and indicate the correct version of the application to be installed. As previously mentioned, the generated message may additionally include a link that the user can click on to download, via the updater 222, the required version of the application. The generated message may also include unexpected software that was found that needs to be uninstalled or removed.

Figure 8:
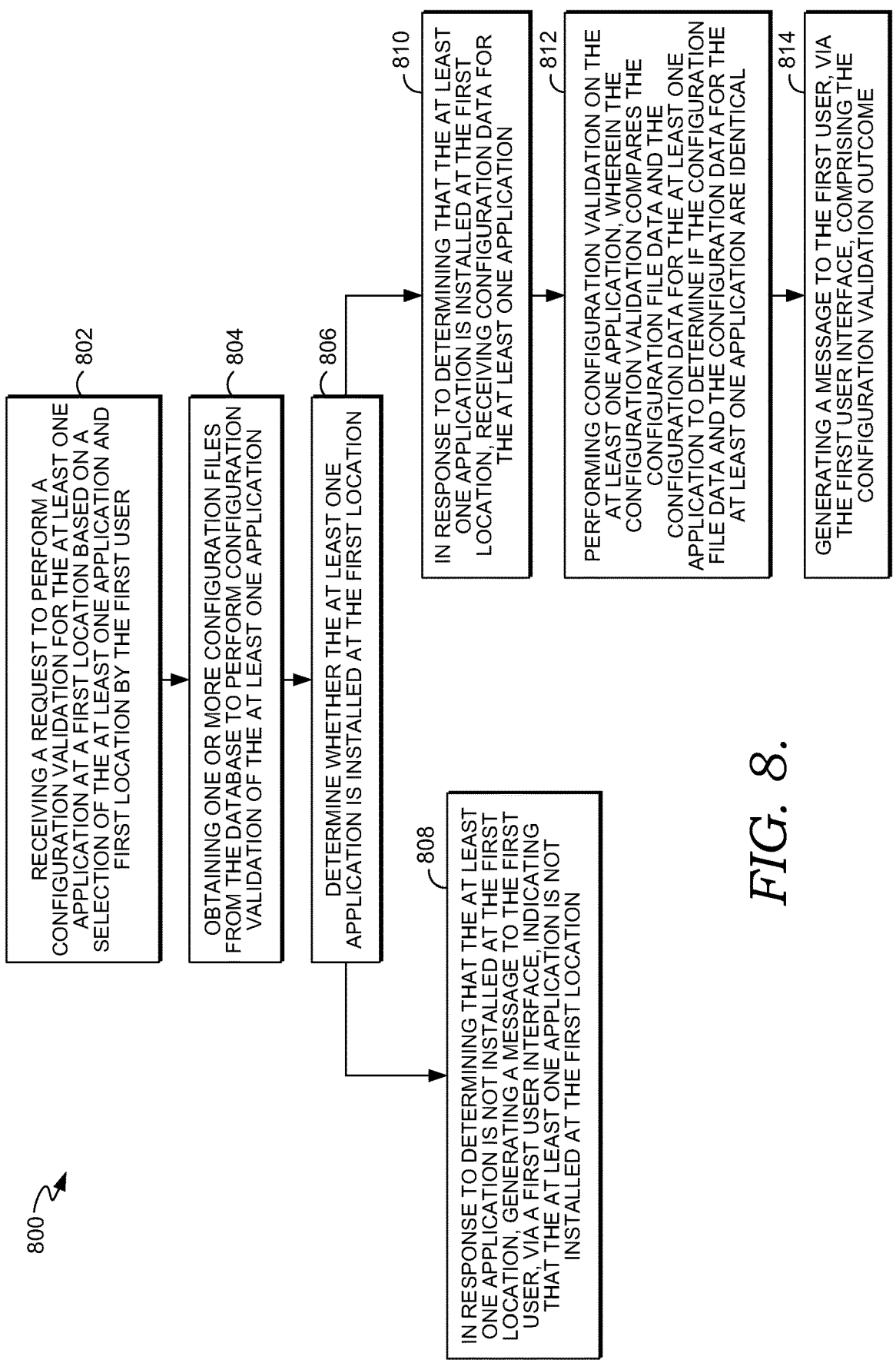
FIG. 8 is a flow diagram describing another example method of executing embodiments of the present invention.

FIG. 8 illustrates another exemplary flow diagram 800 depicting an exemplary method of executing embodiments of the present invention. Beginning with block 802, the receiver 212 receives a request to perform a configuration validation for the at least one application at a first location based on a selection of the at least one application and first location by the first user. Then one or more configuration files may be obtained from database 204 to perform the configuration validation of the at least one application 210 at the first location at block 804. The determiner 228 will determine whether the at least one application is installed at the first location at block 804. If the determiner 228 determines that the application is not installed at the first location, the generator 220 will generate a message to the first user indicating that the application is not installed at the first location at 808. The first user may then install the necessary application and then request a subsequent configuration validation to be conducted to confirm that the version of the application installed is correct. By contrast, if the determiner 228 determines that the at least one application is installed at the first location at block 810, then the application accessor will receive configuration data for the at least one application. The configuration validator will 216 perform a configuration validation on the application in which the configuration validator 218 will compare the configuration file data to the configuration data for the first application to determine if the two are identical at block 812. Then the generator 220 will generate a message to the first user, via the first user's interface, indicating the outcome of the configuration validation performed at block 814.

While blocks 802-814 present the method in the order discussed above, system 200 is adaptable and intelligent and as such, the presented method is exemplary and variations in the order are contemplated herein.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A dynamic system useful for validating the configuration of one or more applications to be used by one or more users in a healthcare management system, the system comprising:

one or more processors configured to:
receive a request to perform a configuration validation for at least one application at a first location;
access a first source to obtain one configuration file comprised of data, the data defining one or more requirements for each particular location type of a client server, a solution server, and a comprehensive server, the one configuration file being specific to the at least one application;
determine that the at least one application is present at the first location based on the one configuration file;
determine the particular location type of the first location;
determine the one or more requirements defined in the one configuration file to use for the particular type of the first location;
access the at least one application at the first location to obtain configuration data for the at least one application;
perform the configuration validation on the at least one application at the first location by determining whether the one or more requirements defined in the one configuration file that are specific to the particular location type of the first location are satisfied based on the configuration data from the at least one application; and generate a message to a first user, via a first user interface, indicating an outcome of the configuration validation.

2. The system of claim 1, wherein the first location is determined to be on one of a client server, solution server, or a comprehensive server.

3. The system of claim 1, wherein the one or more requirements are satisfied when the data in the one configuration file and the configuration data for the at least one application are identical.

4. The system of claim 3, wherein when the one or more requirements are satisfied, the message generated indicates that a correct version of the at least one application is installed.

5. The system of claim 1, wherein the one or more requirements are not satisfied when the data in the configuration file and the configuration data from the at least one application are not identical.

6. The system of claim 5, wherein the message generated indicates that a wrong version of the at least one application is installed and identifies a correct version of the at least one application to be installed.

7. The system of claim 6, wherein the system further provides, via the first user interface, a link to download the correct version of the at least one application.

8. The system of claim 6, wherein the system further automatically updates the at least one application to the correct version.

9. The system of claim 1, wherein the system further identifies at least one additional application located at the first location to be removed.

10. The system of claim 9, wherein the message to the first user indicates that the at least one additional application has been identified for removal.

11. The system of claim 10, wherein the system further automatically removes the at least one additional application.

12. The system of claim 1, wherein the configuration validation outcome is stored in the database for future use.

13. A dynamic system useful for validating the configuration of at least one application to be used by one or more users, the system comprising:
- a database comprising one or more configuration files comprising data that defines one or more requirements for at least one application for each location type of a client server, a solution server, and a comprehensive server;
- one or more processors; and
- a storage device storing a computer program product comprising computer instructions that, upon execution by the one or more processors, cause the one or more processors to perform operations comprising:
  - receiving, from a first user, a request to perform a configuration validation for the at least one application at a first location based on a selection of the at least one application and the first location by the first user;
  - obtaining one of the one or more configuration files from the database to perform the configuration validation on the at least one application, the one configuration file being specific to the at least one application, and the one configuration file defining data, the data defining one or more requirements for each particular location type of a client server, a solution server, and a comprehensive server for the at least one application;
  - determining whether the at least one application is installed at the first location;
  - in response to determining that the at least one application is installed at the first location, receiving configuration data for the at least one application;
  - determining the particular location type of the first location;
  - performing the configuration validation on the at least one application at the first location by determining whether the one or more requirements defined in the one configuration file that are specific to the location type of the first location are satisfied by configuration data for the at least one application based on a comparison; and
  - generating a message to the first user, via the first user interface, comprising a configuration validation outcome.

14. The system of claim 13, wherein the system performs the configuration validation on a predetermined schedule.

15. The system of claim 13, wherein the data regarding the one or more requirements from the one configuration file and the configuration data for the at least one application are in JSON format.

16. The system of claim 13, wherein the configuration validation outcome is stored in the database for future use.

17. The system of claim 13, wherein when the configuration validation determines that the data regarding the one or more requirements from the one configuration file and the configuration data for the at least one application are identical, the message generated indicates that the at least one application is correctly installed.

18. The system of claim 13, wherein when the configuration validation determines that the data regarding the one or more requirements from the one or more configuration file and the configuration data for the at least one application are not identical, the message generated identifies a required version of the at least one application to be installed.

19. A method carried out by a validation configuration tool on a computer healthcare system for validating the configuration of at least one application to be used by one or more users, the method comprising:
- receiving a request to perform a configuration validation for at least one application at a first location;
- accessing a first source to obtain one configuration file comprised of data, the data defining one or more requirements for each particular location type of a client server, a solution server, and a comprehensive server, wherein the one or more requirements for each location type include an application identifier, a version identifier, and an application function, and wherein the one configuration file is specific to the at least one application;
- determining that the at least one application is present at the first location based on the one configuration file;
- determining the particular location type of the first location;
- determining the one or more requirements defined in the one configuration file to use for the particular type of the first location;
- accessing the at least one application to obtain configuration data for the at least one application;
- performing the configuration validation on the at least one application by determining whether the one or more requirements defined in the one configuration file data that are specific to the particular location type of the first location are satisfied based on the configuration data from the at least one application; and generating a message to a first user, via a first user interface, indicating an outcome of the configuration validation.

20. The method of claim 19, wherein the one or more requirements are satisfied when the data of the one configuration file and the configuration data from the at least one application are identical.

\* \* \* \* \*